US00PP08413P

United States Patent [19]

Twomey

[11] Patent Number: Plant 8,413

[45] Date of Patent: Oct. 12, 1993

[54] GRANDIFLORA ROSE PLANT NAMED TWOETERN

[75] Inventor: Jerry Twomey, Leucadia, Calif.

[73] Assignee: DeVor Nurseries, Inc., Watsonville, Calif.

[21] Appl. No.: 944,448

[22] Filed: Sep. 14, 1992

[51] Int. Cl.[5] ..... A01H 5/00

[52] U.S. Cl. ..... Plt./20

[58] Field of Search ..... Plt./28, 11, 20, 22

*Primary Examiner*—Howard J. Locker
*Assistant Examiner*—Elizabeth C. Kemmerer
*Attorney, Agent, or Firm*—Christie, Parker & Hale

[57] ABSTRACT

A new variety of grandiflora rose plant producing red blend flowers.

1 Drawing Sheet

SUMMARY OF THE INVENTION

The present invention relates to a new and distinct variety of rose plant of the grandiflora rose class which was originated by my crossing as seed parent the variety known as 'Gitte' and as pollen parent an unnamed and unpatented seedling of my creation. The varietal denomination of this new rose is 'Twoetern'.

Among the novel characteristics possessed by this new variety which disinguishes it from its parents and all other varieties of which I am aware are its red blend flowers which bloom in small clusters.

Asexual reproduction by budding and rooting of cuttings of the new variety as performed in Watsonville, Calif., shows that the foregoing and other distinguishing characteristics come true to form and are established and transmitted through succeeding propagations.

BRIEF DESCRIPTION OF ILLUSTRATIONS

The accompanying illustration shows typical specimens of the flowers and vegetative growth of the new variety depicted in color as nearly true as it is reasonably possible to make the same in a color illustrations of this character. Phenotypic expression, including colors, may vary depending upon growing conditions, such as climate, soil, and cultivation conditions.

DESCRIPTION OF THE NEW VARIETY

'Twoetern' is a very vigorous healthy growing plant that has dark green glossy foliage that is very resistant to blackspot. The buds and open flower are hybrid tea size on a grandiflora bush. The red blend blooms are presented in clusters upon strong stems. All of the attractive features of this variety are further supplemented by the presence of a pleasing fragrance.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.
*Seed parent.*—'Gitte'.
*Pollen parent.*—Unnamed seedling.
Class: Grandiflora.

The following information is from observations made of specimens grown outdoors in Watsonville, Calif. in the months of May–November.

FLOWER

Blooming habit: Recurrent.

A. Bud:
(1) *Size.*—Small.
(2) *Form.*—Globular.
(3) *Color.*—As sepals divide, bud color is near 45D to C.
(4) *Sepals.*—Pointed, longer than bud, foliated. Color: Near 138B.
(5) *Peduncle.*—Length: About 7 cm to 7.5 cm. Aspect: Slightly curved. Strength: Sturdy, erect. Color: Near 146D.
(6) *Bracts.*—Number — About 3–4. Color — Near 147A. Form — Broadly lanceolate with caudate apex. Location in relation to flower — About 6 to 7 cm below calyx tube.

B. Bloom:
(1) *Size.*—About 10 to 12 cm.
(2) *Borne.*—Clusters of up to 5 blooms.
(3) *Form.*—Imbricated, becoming ruffled at maturity.
(4) *Petalage.*—Number of petals under normal conditions — about 32 to 36.
(5) *Color.*—After sepals fall and flower opens, top side petal coloration is from near 45A at petal margin lightening to near 43D, 39C and 39D toward petal base with intervening zone of near white ending in yellow coloration at point of petal attachment; blooms about ½ open appear generally near 42A to B but become more red to red-purple as blooms age. Petal undersurface resembles petal top surface in zonal colorations but reds tend to be lighter toned and pinks paler. Yellow coloration at point of petal attachment less visible on petal underside.

C. Petals:
(1) *Texture.*—Strong, thick.
(2) *Appearance.*—Inside velvety/satiny; outside semi-satiny.
(3) *Form.*—Broad.
(4) *Arrangement.*—Imbricated.
(5) *Petaloids in center.*—Few.
(6) *Persistence.*—Petals drop off cleanly.
(5) *Fragrance.*—Moderate old rose fragrance.
(6) *Lasting. quality.*—Long lasting on plant.

REPRODUCTION ORGANS

A. Stamens, filaments and anthers:

*Arrangement.*—Irregularly arranged, antrorse anthers.

*Stamens color.*—Near 17A around edges, near 160D in center.

*Filaments.*—Color — Near 9A.

*Anthers.*—Color — Near 17A around edges and near 160D in center.

*Pollen.*—Color — Near 17A.

B. Styles: Protruding, free and separate, uneven length.

*Stigmas.*—Color — Near 13B.

PLANT

A. Form: Tall, upright.

B. Growth: Very vigorous.

*Height attained (first season).*—About 158 to 183 cm in height and 90–100 cm in width.

C. Foliage: Compound 3 to 7 leaflets.

(1) *Size.*—Medium.

(2) *Quantity.*—Abundant.

(3) *Color.*—New foliage: Upper side — Near 147A. Underside — Near 194A. Old foliage: Upper side — Near 147A. Underside — Near 147C.

(4) *Shape.*—Oval, with obtuse base.

(5) *Texture.*—Upper side is leathery and underside is leathery.

(6) *Edge.*—Serrated.

(7) *Serration.*—Serrate.

(8) *Petiole color.*—Top surface — Near 146D. Underside — Near 145B.

(9) *Stipules.*—Slightly bearded, medium length.

(10) *Auricle.*—Long, slender with fine hair.

(11) *Rachis.*—Small prickles underneath.

(12) *Resistance to disease.*—Average resistance to mildew and rust. Very resistant to blackspot.

C. Wood (1) *New wood.*—Color — Near 144A. Bark — Smooth.

(2) *Old wood.*—Color — Near 137C. Bark — Smooth.

(3) *Flower stem length from last cutting.*—About 40 to 46 cm.

E. Thorns:

*Quantity (main stalk).*—Ordinary.

*On laterals from stalk.*—Ordinary.

*Form.*—Curved downwardly, slightly hooked.

*Length.*—Medium.

*Position.*—Irregular.

*Prickles.*—Many.

F. Winter hardiness: Moderately winter hardy.

I claim:

1. A new and distinct variety of rose plant of the grandiflora rose class, substantially as shown and described.

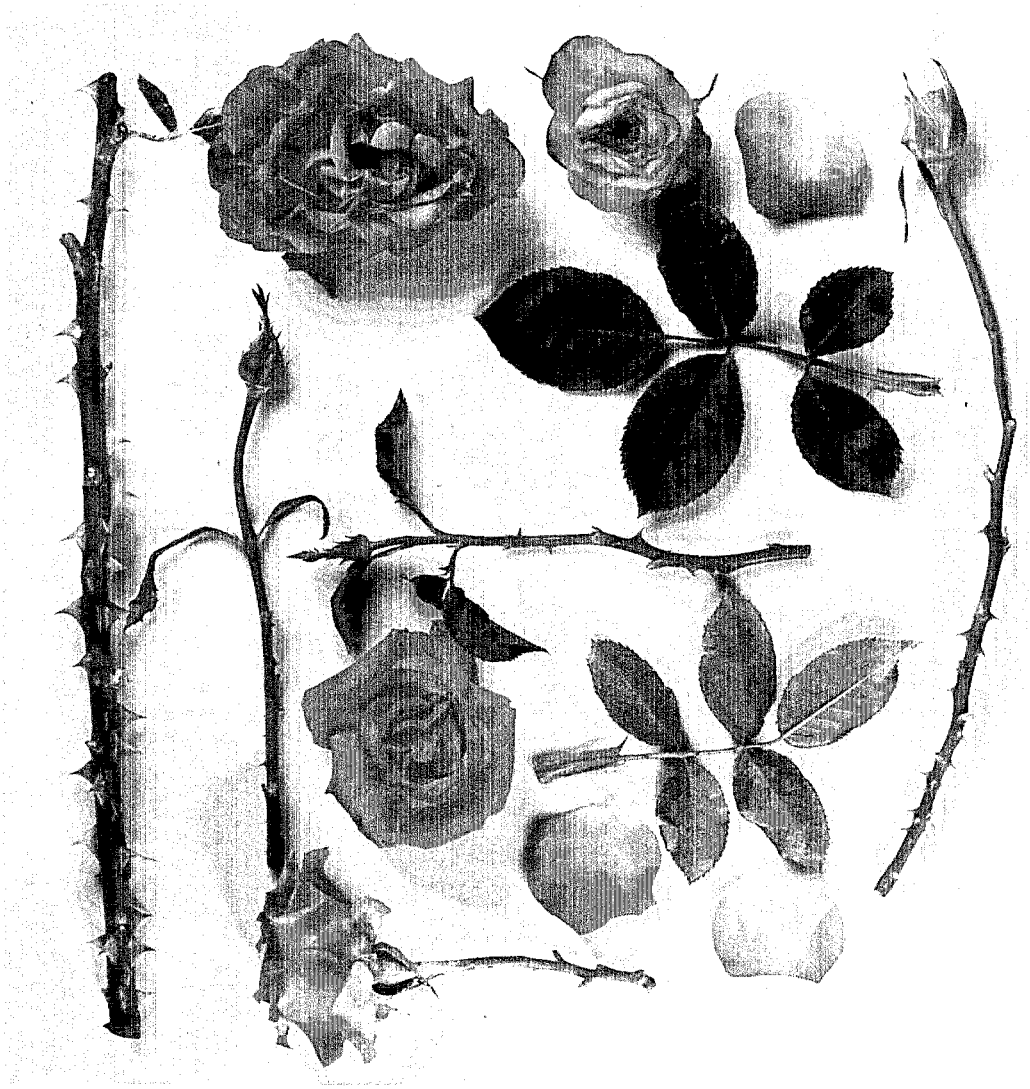

* * * * *